(12) United States Patent
Fan (10) Patent No.: US 10,405,852 B1
(45) Date of Patent: Sep. 10, 2019

(54) PUSH-TWIST SUTURE-PASSING LAPAROSCOPIC KNOT TYING INSTRUMENT

(71) Applicant: Peter Fan, Englewood Cliffs, NJ (US)

(72) Inventor: Peter Fan, Englewood Cliffs, NJ (US)

( * ) Notice: Subject to any disclaimer, the term of this patent is extended or adjusted under 35 U.S.C. 154(b) by 0 days.

(21) Appl. No.: 16/010,601

(22) Filed: Jun. 18, 2018

(51) Int. Cl.
  *A61B 17/04* (2006.01)
  *A61B 17/00* (2006.01)
(52) U.S. Cl.
  CPC .......... *A61B 17/0469* (2013.01); *A61B 2017/00367* (2013.01); *A61B 2017/00477* (2013.01)
(58) Field of Classification Search
  CPC ............ A61B 2017/2906; A61B 17/28; A61B 17/2812; A61B 17/2841; A61B 17/29; A61B 2017/2901; A61B 2017/2902; A61B 2017/2903; A61B 17/2909; A61B 2017/2912; A61B 2017/2913; A61B 2017/2915; A61B 2017/2916; A61B 17/0469
  See application file for complete search history.

(56) References Cited

U.S. PATENT DOCUMENTS

| | | | | |
|---|---|---|---|---|
| 5,336,230 A | * | 8/1994 | Leichtling | A61B 17/0469 128/898 |
| 5,759,188 A | * | 6/1998 | Yoon | A61B 17/0469 606/147 |
| 7,998,149 B2 | * | 8/2011 | Hamilton | A61B 17/062 606/144 |
| 2012/0239080 A1 | * | 9/2012 | Fan | A61B 17/0469 606/205 |
| 2018/0125480 A1 | * | 5/2018 | Fan | A61B 17/0483 |

* cited by examiner

*Primary Examiner* — Thomas M McEvoy (57) ABSTRACT

This is a laparoscopic instrument intended to facilitate intra-corporeal tying of knots in a free strand of suture. The shafts of two small diameter laparoscopic graspers are combined within a common external sheath, and both are joined to a common handle to be used by one hand. One grasper has a regular scissors type of handle, is stationary, and acts as a recipient grasper, while the other grasper has no handle, but is able to rotate and to slide, and acts as a donor grasper. The instrument enables the head end of a suture to be actively passed from the donor grasper to the adjacent recipient grasper, passing behind and around the tail strand, forming a knot, in the same manner as in the tying of shoes-laces. The current instrument introduces a new mechanism, whereby the required rotational movements are automatically produced by the sliding motion.

2 Claims, 13 Drawing Sheets

PUSH-TWIST SUTURE-PASSING LAPAROSCOPIC KNOT TYING INSTRUMENT

FIELD OF THE INVENTION

The tying of knots in a suture intra-corporeally with laparoscopic instruments is difficult and time consuming. Surgeons are still in need of an instrument that would facilitate this tying process. The present device combines two graspers in one instrument to be used in one hand and enables the passing of the head end of a suture from a donor grasper to an adjacent recipient grasper behind the tail end of the same suture, thereby creating the knot.

BACKGROUND OF THE INVENTION

Tying of knots is essential in any kind of surgery. It is relatively easy in open surgery but is difficult in laparoscopic surgery. The current art of laparoscopic knot tying employs either the extra-corporeal method, involving tying the knot by hand outside the body and pushing the knot inside with a knot pusher, or the intra-corporeal method, involving manipulation of the suture with the tips of two laparoscopic graspers, which is slow and cumbersome, and requires considerable skill. Laparoscopic clip appliers, staplers, pre-tied knots and the like are useful substitutes, but cannot totally replace tied knots which are still needed. Despite considerable prior art, today hardly any hand operated instrument exists that renders laparoscopic intra-corporeal knot tying easier and faster.

Figure 1:
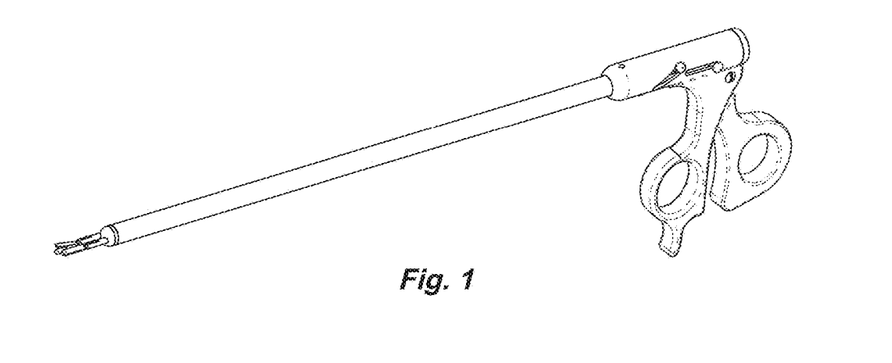
FIG. 1 is a perspective view of the entire instrument from the left side.
Figure 2:
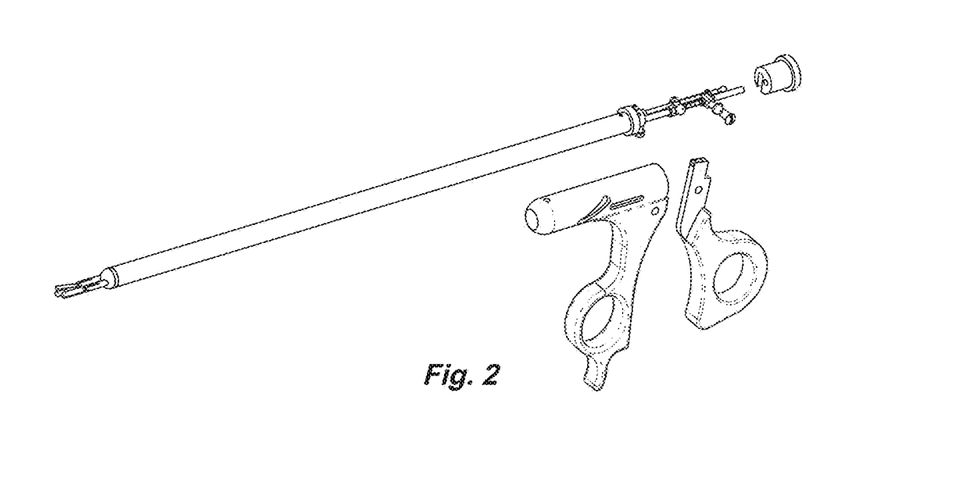
FIG. 2 is an exploded view of the handle end of the instrument.
Figure 3:
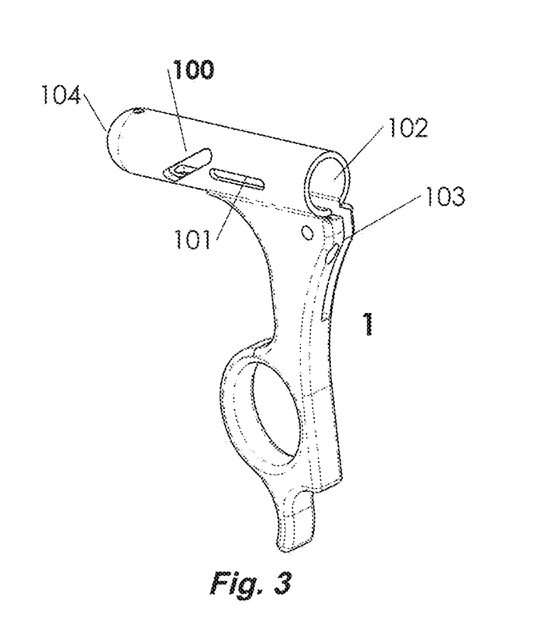
FIG. 3 is a perspective view of the stationary handle. The feature 100 is an angled slot on the left side of the tubular chamber on the top of the stationary handle, for the rotating lever 9. 101 is a horizontal slot. 102 is the entrance to the rear of the chamber for entry of the main sheath sub-assembly. 103 is an open vertical slot on the backside of the stationary handle for hiding the upper limb of the movable handle.
Figure 4:
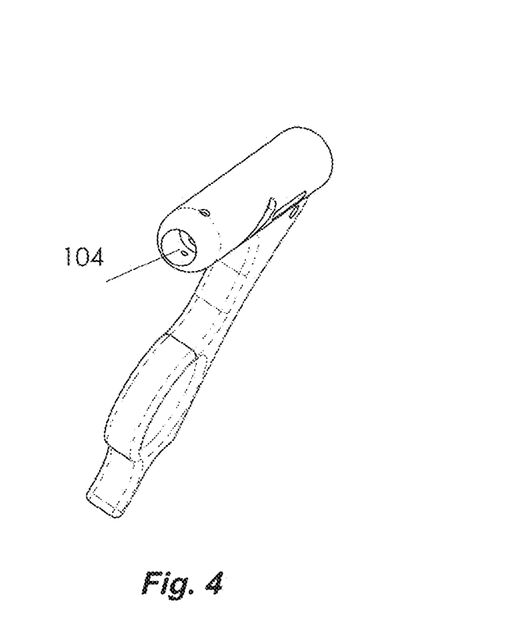
FIG. 4 is another perspective view of the stationary handle. 104 is a large opening at the front end of the chamber, for exit of the front end of the main sheath sub-assembly.
Figure 5:
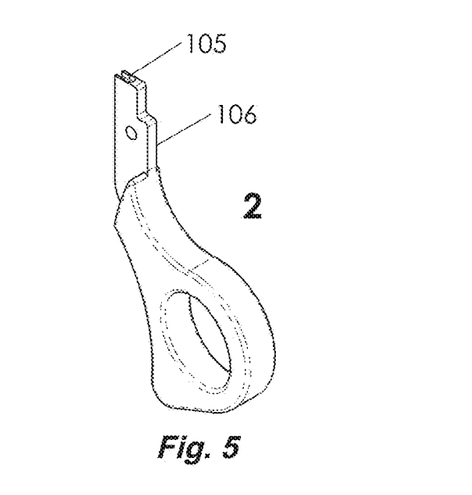
FIG. 5 is a perspective view of the movable handle. 105 is a receptacle for the ball to form the ball-joint. 106 is a narrow upper stem of the movable handle, with a cut out.
Figure 6:
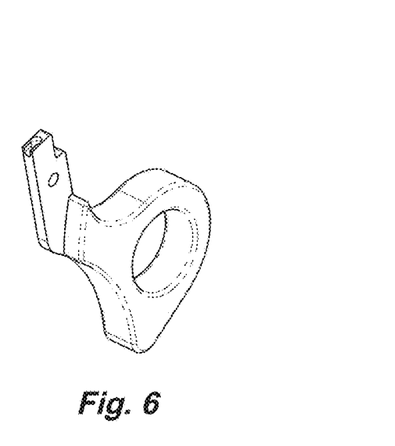
FIG. 6 is another perspective view of the movable handle.
Figure 7:
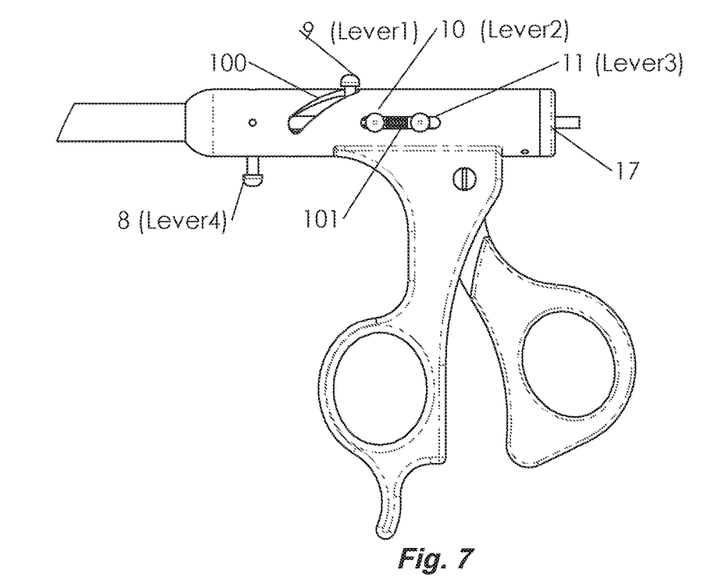
FIG. 7 is a left side view of the two handles. Feature 100 is the angled slot for controlling rotation of the donor grasper. 6 is the rotating lever. 101 is the horizontal slot for forward and backward sliding of the donor grasper. 7 is the sliding lever with a free-wheeling attachment to the donor grasper's rod. 17 is the rear plug.
Figure 8:
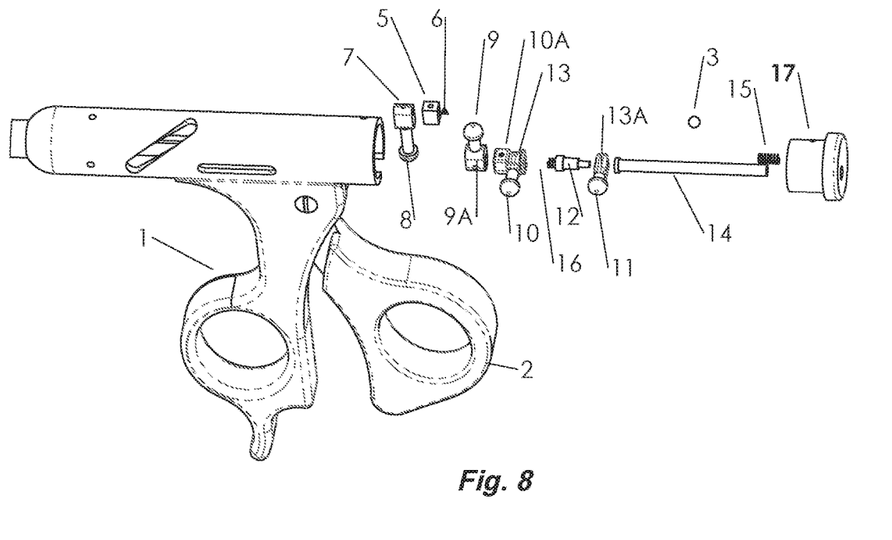
Figure 9:
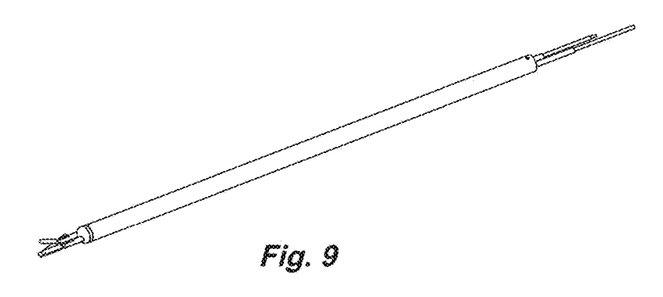
FIG. 9—shows the main sheath sub-assembly, minus the two handles.
Figure 10:
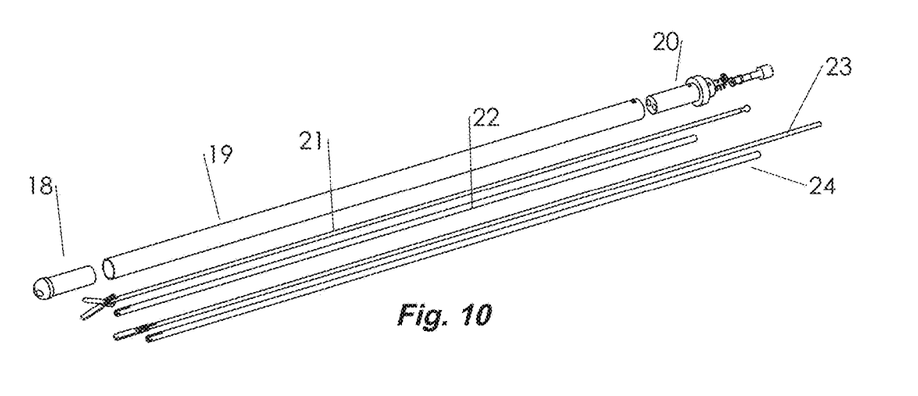
FIG. 10—shows an exploded view of the main sheath sub-assembly, showing its numerous components. 18 is the front spacer. 19 is the main sheath. 20 is the rear spacer. 21 is the right rod whose right end is attached to a ball. 22 is the right sheath. 23 is the left rod, whose right end is attached to the Rod-extension2. 24 is the left sheath.
Figure 11:
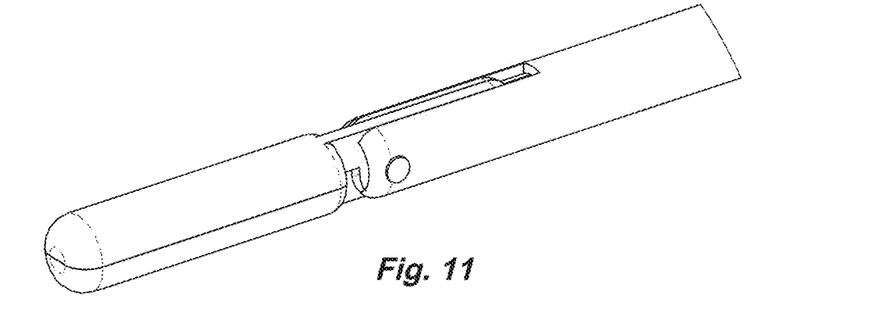
FIG. 11—shows both jaws closed.
Figure 12:
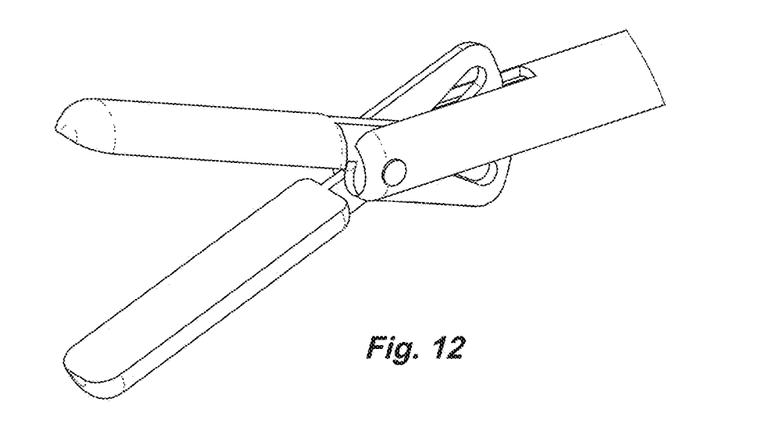
FIG. 12—shows both jaws fully opened to 45 degrees.
Figure 13:
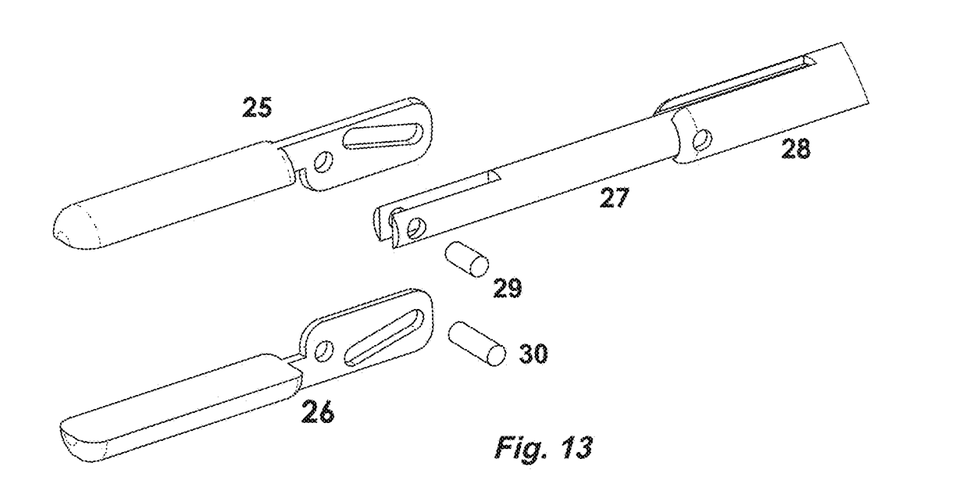
FIG. 13—shows the components of the 45-degree jaw exploded. 25 is the upper jaw. 26 is the lower jaw, which is identical to the upper jaw. 27 is the rod whose tip is modified to accept the jaws. 28 is the sheath whose tip is similarly modified to accept the jaws.
Figure 14:
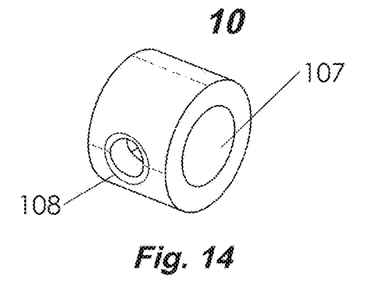
FIG. 14 shows the Adaptor-3, part #10, with 107 for the sheath, and 108 for the Lever
Figure 15:
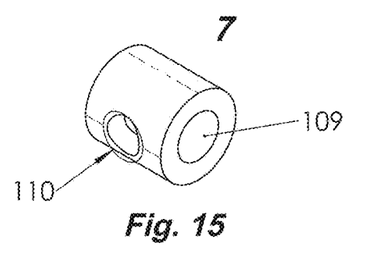
FIG. 15 shows the Adaptor-1, part #7, with 109 for the rod, and 110 for the min-screw.
Figure 16:
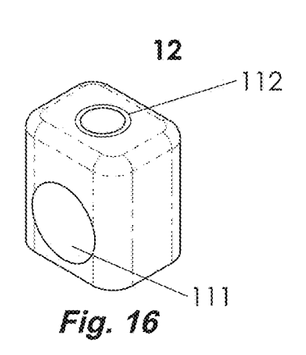
FIG. 16 shows the free-wheeling Adaptor-4, #12, with 111 larger than the diameter of sheath.
Figure 17:
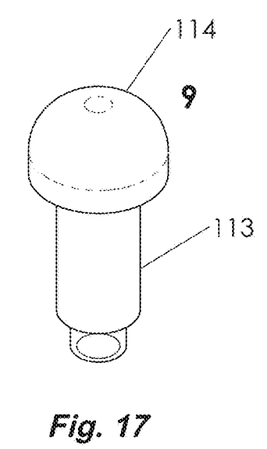
FIG. 17 shows the Rotation-Lever, #9, which screws into 108.
Figure 18:
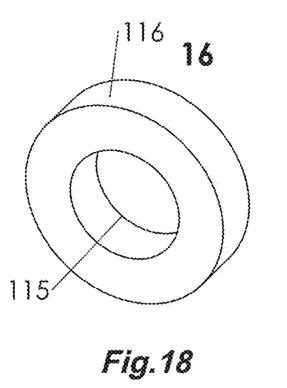
FIG. 18 is a Washer #16, for retaining the spring.
Figure 19:
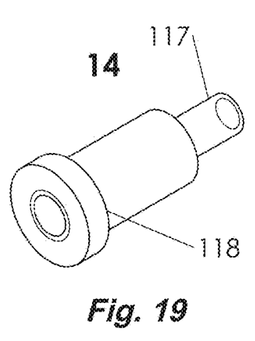
FIG. 19 is the short Rod-Extension2, whose male thread 117 screws into the female thread 119 of part #13.
Figure 20:
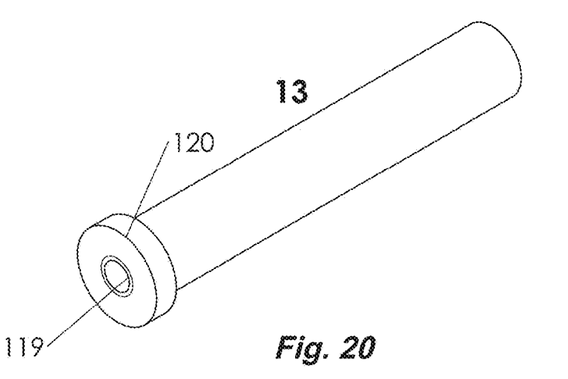
FIG. 20 is the long Rod-Extension, part #13. Both rod extensions have a flange, 118 and 120 which are used to retain the free wheel Adaptor.
Figure 21:
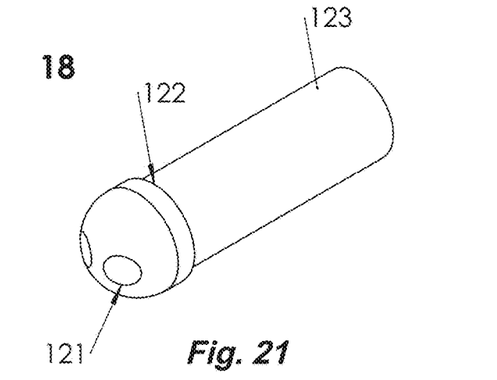
FIG. 21 shows the Front Spacer. Part #18. 121 is a channel for the sheath of a grasper. 122 is a flange. 123 is the shaft.
Figure 22:
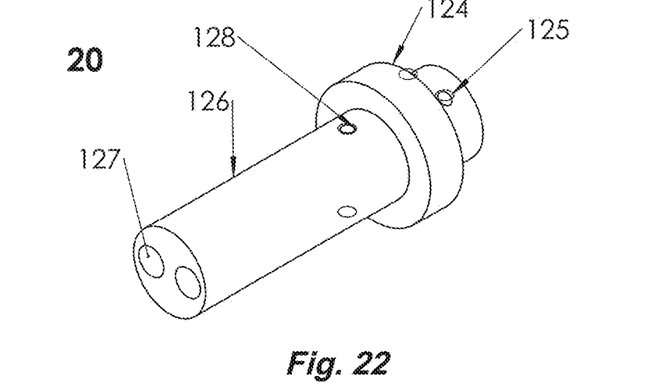
FIG. 22 shows the Rear Spacer, Part #20. 124 is the flange. 125 is a threaded hole for locking the sheath of the grasper. 126 is the shaft. 127 is a tunnel. 128 is for mounting mini-screw.
Figure 23:
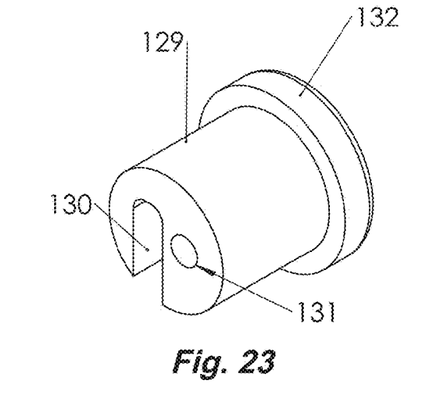
FIGS. 23 & 24 show perspective views of the Rear Plug, part #17, which is the last part to be inserted. 129 is the body. 130 is the blind slot to accommodate the upper end of the movable grasper and the ball joint. 131 is the through hole for sliding the rod-extension back and forth. 132 is the flange closing the tubular chamber.
Figure 24:
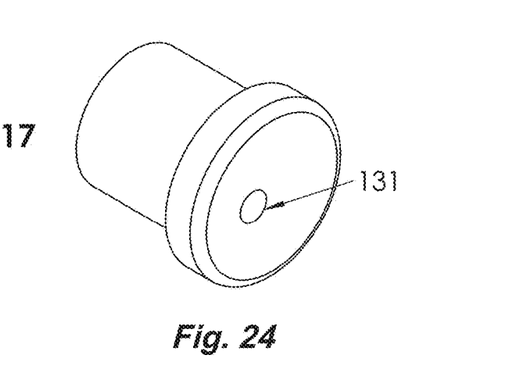
Figure 25:
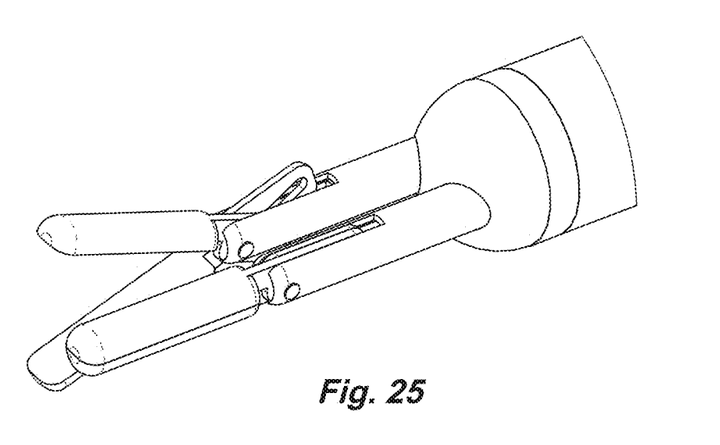
FIG. 25 shows the resting positions of the jaws of the instrument, one open, one closed.
Figure 26:
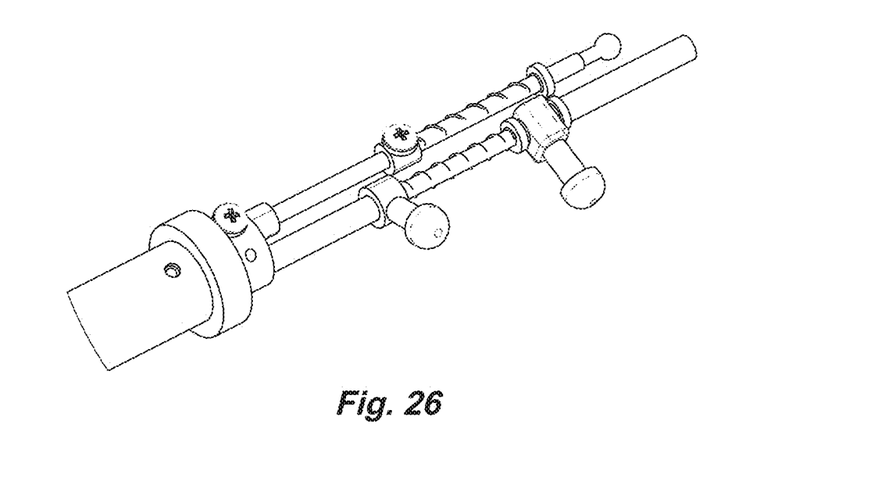
FIG. 26 shows the detailed mechanisms inside the tubular chamber at the top of the instrument.
Figure 27:
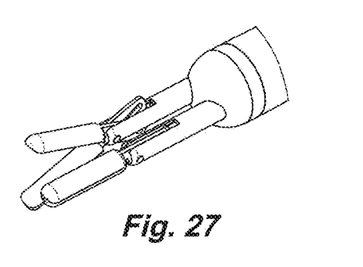
FIG. 27 shows the jaw positions at rest.
Figures 28, 30:
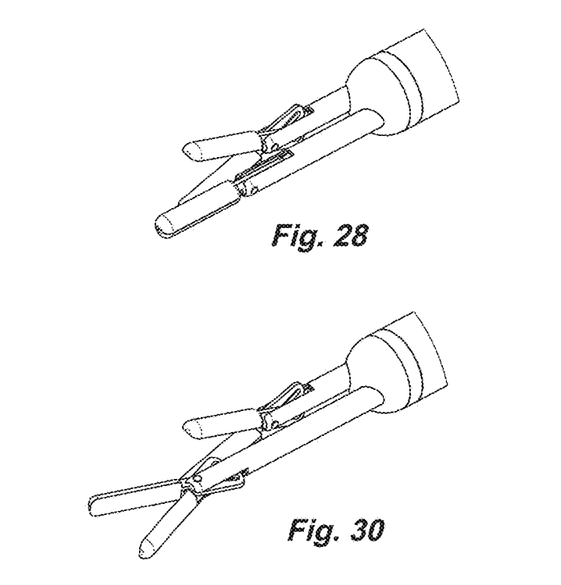
FIG. 28 shows the donor grasper extended.
FIG. 30 shows the vertical jaws opening.
Figure 29:
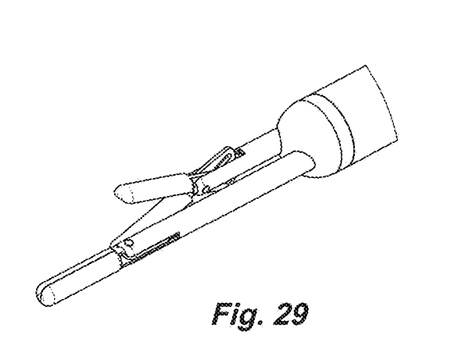
FIG. 29 shows the jaws rotating to the vertical position.
Figure 31:
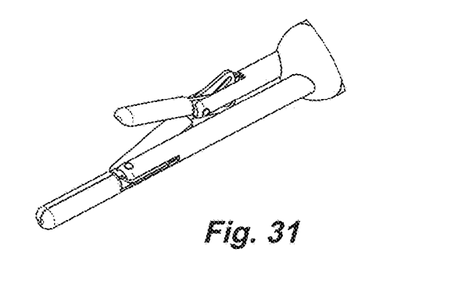
FIG. 31 shows the vertical jaws closing.
Figures 32, 34:
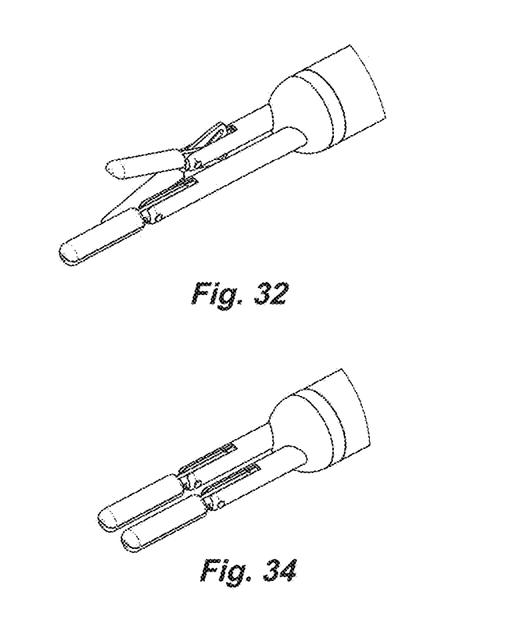
FIG. 32 shows the vertical jaws de-rotating back to horizontal.
FIG. 34 shows the jaws of the recipient grasper closing and taking over.
Figure 33:
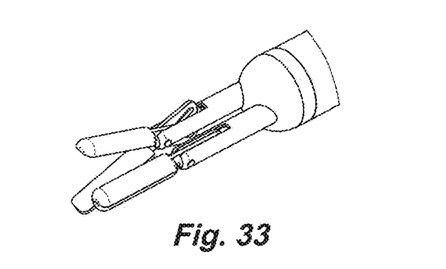
FIG. 33 shows the horizontal jaws returning to original starting position.
Figure 35:
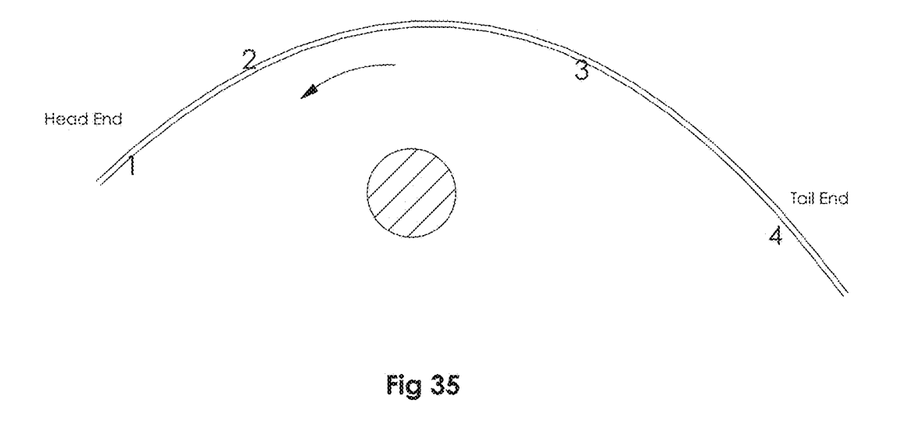
FIG. 35 shows the Naming of the different parts of a suture in the tying process. 1 is the Head End, 2 is the Head Strand, 3 is the Tail Strand, 4 is the Tail End.
Figure 36:
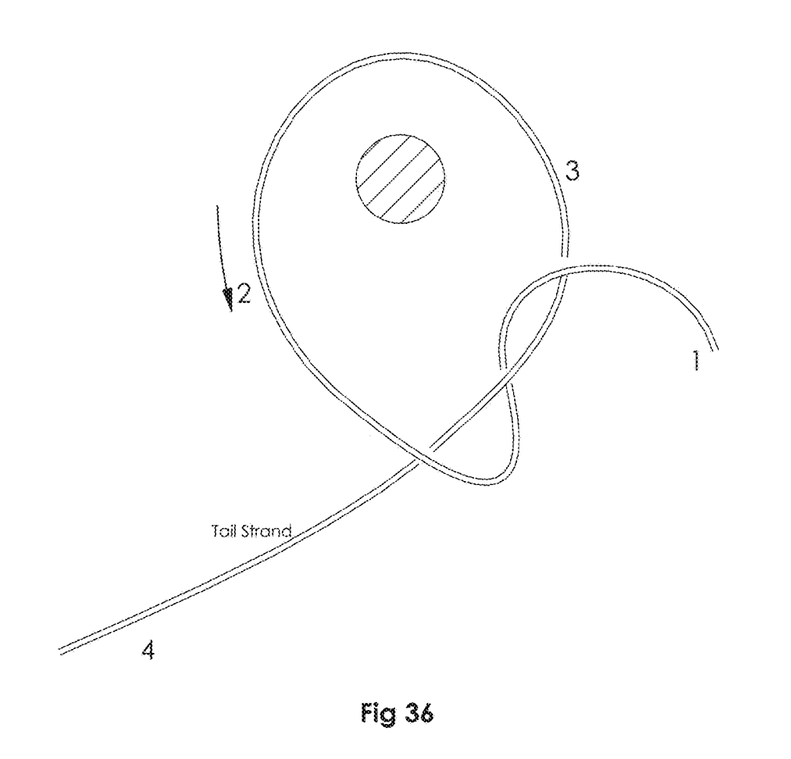
FIG. 36 shows the Head End traveling over, under, and over again the Tail Strand Sheet 11—
Figures 37, 38:
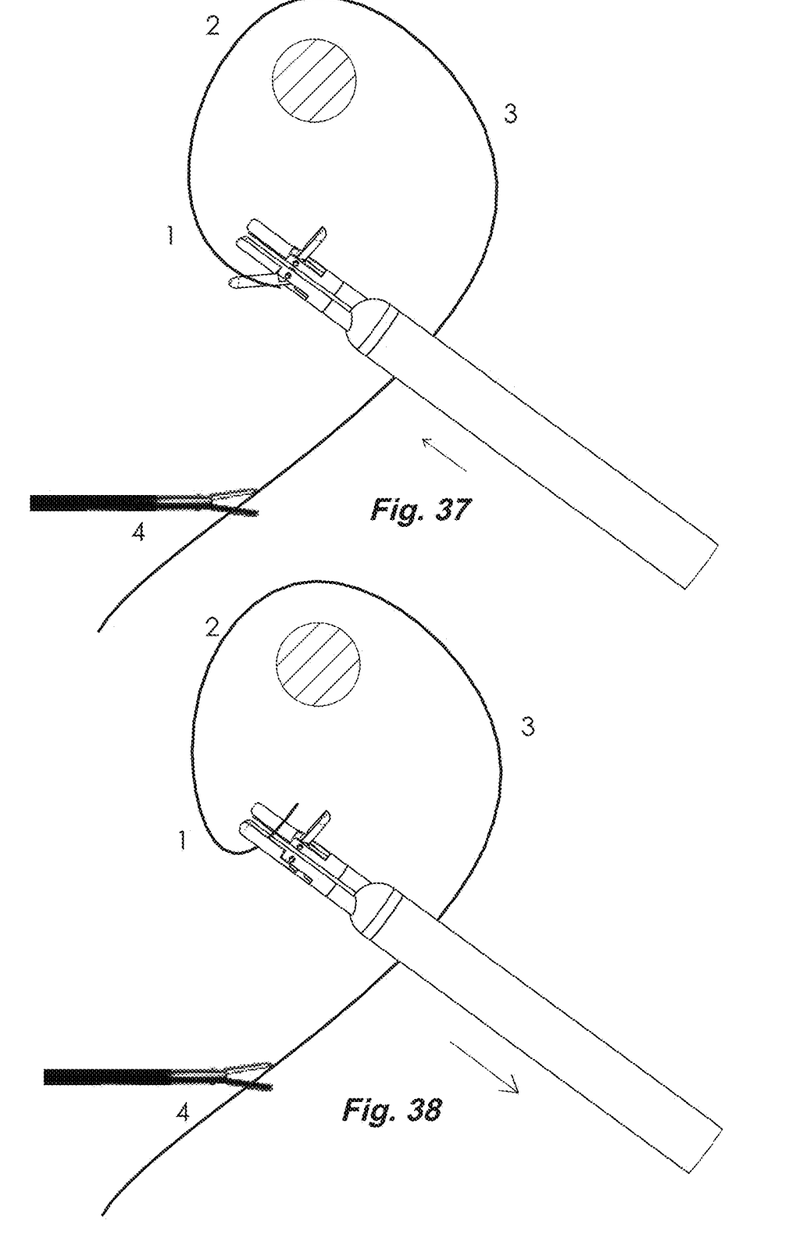
FIG. 37—shows the entire instrument advancing forwards over the tail strand, and grasping the head end of the suture with the jaws of the donor grasper.
FIG. 38—shows pulling back the entire instrument over the tail strand.
Figure 39:
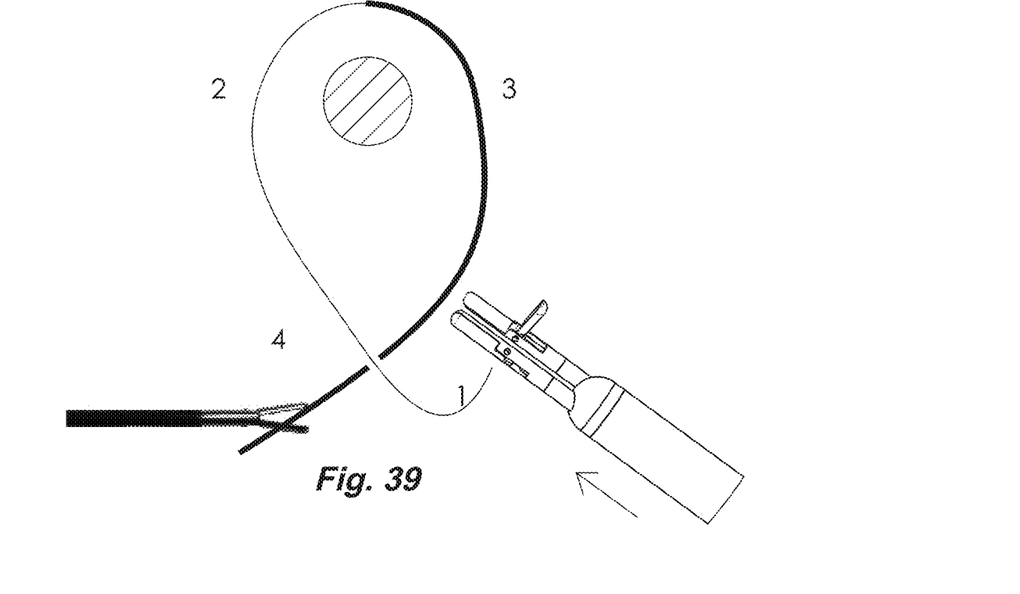
FIG. 39—shows pushing forwards the entire instrument, carrying the head end of the suture with it, and trapping the tail strand in the gap between the tips of the two graspers, with the donor grasper on the underside.
Figure 40:
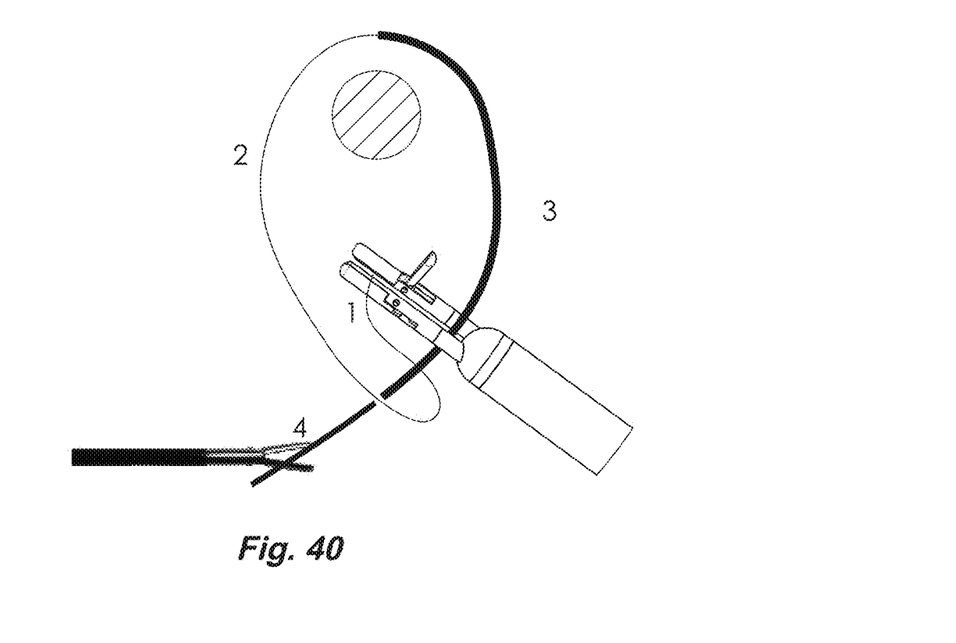
FIG. 40—shows the return of the jaws of the donor grasper to the original position, prior to closing jaws of the recipient grasper.
Figure 41:
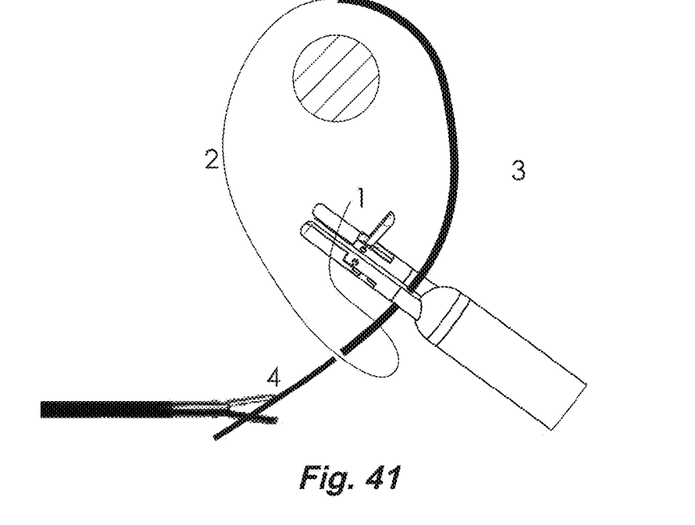
FIG. 41—shows the jaws of the recipient grasper about to close on the head end of the suture.
Figure 42:
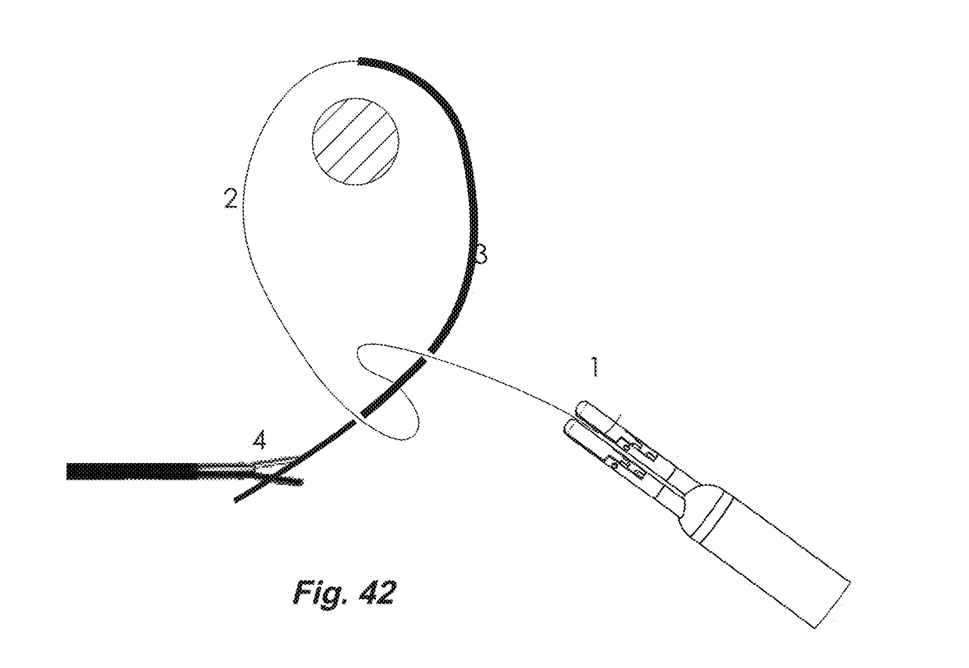
FIG. 42—shows the recipient grasper taking over the head end of the suture and pulling away to form the knot.

In order to describe the tying process, the different parts of a suture ligature need first be given names. As shown in FIG. 18 in the drawings, after the suture ligature has passed around the tissue to be tied, it then presents with a head end (1), a head strand (2), a tail strand (3), and a tail end (4).

There are three basic methods of tying a knot, whether done openly or laparoscopically. The first method makes the head end of the suture pass 360 degrees continuously around the tail strand, as is shown in the U.S. Pat. No. 9,561,028, "Automatic Laparoscopic Knot Tier", invented by this author, and was designed specifically to avoid the release and re-grab.

The second method makes a loop, which is commonly used by surgeons performing open surgery, where the surgeon makes "instrument ties", by wrapping the tail strand of the suture around the needle holder, and then pulling the head end of the suture through the loop. The instrument described in the U.S. Pat. No. 9,820,736, invented also by this author, makes such a loop laparoscopically.

The third method involves making a "throw", which actively passes the head end of the suture behind its tail strand, between two adjacent graspers. This simulates the tying of shoe-laces by fingers and requires the release and re-grab of the head end of the suture, behind the tail strand, which is now the object of the present invention.

In the present invention, two small diameter laparoscopic graspers are incorporated inside a common external sheath, with one being stationary and keeping a regular scissors type of handle, known as the recipient grasper, and the other losing its handle, becoming rotatable, as well as slide-able, known as the donor grasper.

Referring to the author's own previous attempts, the first was the "Double Laparoscopic Grasper", U.S. Ser. No. 13/051,992, which was abandoned because the passing of the suture between the two graspers could not be accomplished at that time. The author's second attempt was the "Automatic Laparoscopic Knot Tying Instrument", U.S. Pat. No. 9,561,028, which uses a mini-grasper at the tip of the instrument grasping the head end of the suture, then rotating through 360 degrees around the tail strand, and avoiding the release and re-grab of the head end of the suture. The author's third attempt was the "Laparoscopic Suture Loop Maker", U.S. Pat. No. 9,820,736, which worked quite well, but also avoided the release and re-grab. However, the $2^{nd}$ and $3^{rd}$ inventions were not fully practicable because, after the knot was made, the final take away depended on springs holding on to the head end of the suture, which proved inadequate. The holding power of the jaws was improved in the $4^{th}$ invention, by incorporating a scissors type of handle and using the power of the thumb, U.S. patent application Ser. No. 15/859,717, which also included the element of rotation, which although worked, was not ideal, because it depended on the use of the unreliable 90-degree jaws. A subsequent Continuation-in-Part added sliding to avoid the use of the 90-degree jaws. The current instrument further improves by automatically producing the rotation during the sliding, and further enables the use of the standard double-acting 45-degree laparoscopic grasper jaws.

Referring to the previous literature, the Christoudias Double Grasper has 3 jaws, with a common middle jaw, but functions as a tissue approximator. Its spring-loaded actuators are operated by two push buttons. The Ferzli Double Grasper, has a second pair of jaws positioned more proximally on the main shaft, whose purpose is to anchor one end of the suture prior to twisting it around the shaft of the instrument in order to produce a loop. The Hasson Suture Tying Forceps, is similar to the Ferzli, with 3 finger loops. The orthopedic suture passers are for passing sutures only through hard tissue, and these include the Arthrex Scorpion Suture Passer, and the Arthrex Birdbeak Suture Passer. Some suture passers are for passing sutures through a thickness of soft tissue such as the abdominal wall, and these include the Goretex and the Aesculap. There are devices which "pass the suture-needle" side to side, for inserting sutures into tissues, as well as for tying knots, e.g. the Autosuture's Endo-stitch, and the Japanese Maniceps. Note these only pass the suture needle, not the suture thread per se. There have been devices that attempt to "automatically" tie a knot, such as Jerrigan's experimental rotating slotted disc designed for robotic endo-cardiac surgery, but it was abandoned because of the requirement for a manufactured cartridge.

There have been also many devices that help to "create a loop", but with each functioning differently—(a) Kitano's grasper with the rotating sleeve, Japanese, (b) Donald Murphy's grasper with the extra horn, Australian, (c) Grice's sleeve catching instrument, (d) Bagnato & Wilson's device which simulates the radiological pig-tail catheter, with a preformed loop built into the tip of the catheter, which is deformable and purportedly a loop former, but it is difficult to manufacture and apply, and has not yet been reduced to practice, (e) Ferzli's double grasper, which anchors one end of the suture, as described above. There have been devices using a "pre-formed knot", (1) Ethicon's Endo-Loop, (2) the Duraknot, (3) LSI's device, (4) Pare's pre-tied knot, all of which do not help to tie knots.

Other past inventions related to intra-corporeal laparoscopic knot tying fail to address the basic problem of "how to create a knot". They usually offer various alternatives, such as making fishing knots, using pre-tied knots, knot pushers, suture clips, cinchers, tissue fasteners, anchors, stapling devices, etc. The present invention however actively passes the head end of the suture behind its tail end, from one grasper to another grasper, to make the actual knot intra-corporeally.

| U.S. PAT. DOCUMENTS | | | | |
|---|---|---|---|---|
| 1. 3,834,395 | Sep. 10, 1974 | Manuel Santos | | 128/326 |
| 2. 5,201,759 | Apr. 13, 1993 | George Ferzli. | | 606/139 |
| 3. 5,217,471 | Jun. 8, 1993 | Stephen Burkhart | | 606/148 |
| 4. 5,234,443 | Aug. 10, 1993 | Phan & Stoller | | 606/148 |
| 5. 5,250,054 | Oct. 5, 1993 | Lehmann Li | | 606/148 |
| 6. 5,281,236 | Jan. 25, 1994 | Bagnato et al. | | 606/139 |
| 7. 5,312,423 | May 17, 1994 | Rosenbluth & Brenneman | | 606/148 |
| 8. 5,395,382 | Mar. 7, 1995 | DiGiovanni et al. | | 606/148 |
| 9. 5,437,682 | Aug. 1, 1995 | Drew Grice | | 606/148 |
| 10. 5,423,836 | Jun. 13, 1995 | Scott Brown | | 606/148 |
| 11. 5,439,467 | Aug. 8, 1995 | Theodore Benderev, et al. | | 606/139 |
| 12. 5,480,406 | Jan. 2, 1996 | Nolan et al. | | 606/139 |
| 13. 5,728,109 | Mar. 17, 1998 | Schulze et al. | | 606/148 |
| 14. 5,810,852 | Sep. 22, 1998 | Greenberg et al. | | 606/148 |
| 15. 5,814,054 | Sep. 29, 1998 | Kortenbach et al. | | 606/139 |
| 16. 5,846,254 | Dec. 8, 1998 | Schulze et al. | | 606/228 |
| 17. 6,051,006 | Apr. 18, 2000 | Shluzas & Sikora | | 606/148 |
| 18. 6,086,601 | Jul. 1, 2000 | InBae Yoon | | 606/148 |
| 19. 6,221,084 | Apr. 24, 2001 | R. Fleenor, Pare Surgical | | 606/148 |
| 20. 6,432,118 | Aug. 13, 2002 | Mollenhauer & Kucklick | | 606/148 |
| 21. 6,716,224 | Apr. 26, 2004 | Singhatat | | 606/148 |
| 22. 2009/0228025 | Sep. 10, 2009 | Steven Benson | | 606/144 |
| 23. 2010/0016883 | Jan. 21, 2010 | George Christoudias | | 606/205 |
| 23. 5,312,423 | May 17, 1994 | Rosenbluth et al. | | 606/148 |
| 25 8,512,362 | Aug. 20, 2013 | Ewers et al. | | 606/158 |
| 26. 4,635,638 | January 1987 | Weintraub. | | |
| 27. 5,938,668 | August 1999 | Scirica | | |
| 28. 5,954,731 | September 1999 | Yoon. | | |
| 29. 6,017,358 | January 2000 | Yoon | | |
| 30. 6,086,601 | July 2000 | Yoon. | | |
| 31. 2008/0228204 | September 2008 | Hamilton. | | |
| 32. 2013/051992 | Sep. 30, 2012 | Fan - Double Laparoscopic Grasper. | | |
| 33. 9,561,028 | Feb. 7, 2017 | Fan - Automatic Lap. Knot Instrument | | |
| 34. 9,820,736 | Nov. 21, 2017 | Fan - Laparoscopic Suture Loop Maker. | | |
| 35. 15/859,717 | Jan. 1, 2018 | Fan - Suture Passing Laparoscopic Knot-tier. | | |

OTHER PUBLICATIONS

1. Endo-stitch—Autosuture—Manufacturer's item #173016.
2. Maniceps—Japanese suturing device, similar to Endo-stitch.
3. A Laparoscopic Device for Minimally Invasive Cardiac Surg. Shaphan Jernigan, et. al.—European J. of Cardiothoracic Surgery, Vol. 37, p. 626-630. March 2010.
4. Knot Tying Intra-corporeally, with newly designed Forceps. (sliding sleeve).
5. Kitano et. al.—J. of Minimal Invasive Therapy & Allied Tech, 1996. 5:27-28.
6. Endoscopic Knot Tying Made Easier—(one jaw with extra bump).
7. Donald Murphy—ANZ J. Surg. 1995. 65, 507-509.
8. The Excalibur Suturing Needle Holder—(jaw with prominent heel, helps looping)
9. Uchida et. al. Surgical Endoscopy—vol. 3, 531-532
10. Alijizawi laparoscopic auto-knot device—(two dissolving balls).
11. A New Reusable Instrument designed for simple and secure knot tying in laparoscopic surgery. S. S. Miller 1996 Surg. Endos 10: 940-941 (pointed canula).
12. The Nobel Automatic Laparoscopic Knotting and Suturing Device. Mishra et. al. World Laparoscopy Hospital, India. (a knot pusher)
13. Automated Knot Tying for Fixation in Minimally Invasive Robot Assisted Cardiac Surgery. March 9(1):105-12.
14. Kuniholm & Buckner—J. Biomed Eng. November 2005, Vol. 127, 1001-8. JSLS.2005 January
15. M I Frecke—Laparoscopic multifunctional instruments: design and testing. Endosc Surg Allied Technol. 1994 December; 2(6):318-9.
16. G. Berci—Multifunctional laparoscopic Instruments.
17. http://www.ligasure.com/ligasure/pages.aspx?page=Products/Laparoscopi
18. http://www.freepatentsonline.com/y2010/0063437.
19. http//www.ncbi.nlm.nih.gov/pubmed/15791983 Multi-functional Laparoscopic Instruments.

SUGGESTED U.S. CLASSIFICATION: 606/139, 144, 145, 148.
SUGGESTED INTERNATIONAL CLASSIFICATION: A61B 17/00, 04, 28.
FIELD OF SEARCH: 606/139, 144, 145, 147, 148, 150, 151, 127, 128, 606/167, 168, 170, 174, 182, 185, 205, 207, 210, 211.
RELATED PRIOR PATENTS: 2013/051,992 U.S. Pat. No. 9,194,468. 9,561,028. 9,820,736.

SUMMARY OF THE INVENTION

In laparoscopic surgery, the tying of knots intra-corporeally is typically performed manually using the tips of two graspers. It is still technically difficult and requires considerable skill and practice. The advent of laparoscopic clips and staples has been a great blessing to surgeons, but cannot totally replace the use of tied knots, which is still necessary. The instrument presented here not only enables the passing of the head end of suture between two adjacent graspers, behind and around the tail end of the suture, but allows the use of the simple double-acting 45-degree laparoscopic jaws, and in addition, introduces a mechanism that automatically creates the necessary simultaneous rotation during the sliding of the handle-less grasper, simplifying the maneuvers. It conforms to the customary shape and size of a laparoscopic instrument, with an elongated round sheath, a regular scissors type of handle at the proximal end, and two small diameter grasper tips protruding at the distal end. The jaws of one of the graspers are controlled manually, and the jaws of the other by compression springs. The main grasper, known as the recipient grasper, is stationary and non-mobile, and behaves like a regular grasper, with the advantage of using the thumb pressure during the final take-away, while the secondary grasper, known as the donor grasper is without a handle, and is rotatable and slide-able. This combination of the two mini-graspers, one with a handle and one without, enables the passing of the suture from one grasper to another, and is the heart of this device. All the manipulations are performed by the thumb at the handle, namely: opening the jaws of the donor grasper, rotating and sliding the entire donor grasper, and closing the upper jaw of the recipient grasper.

| PART NUMBERS AND NAMES | |
|---|---|
| 1. | Stationary Handle. |
| 2. | Movable Handle. |
| 3. | Ball. |
| 4. | Retaining Washer |
| 5. | Mini-Screw-1 |
| 6. | Adaptor-1. |
| 7. | Adaptor-2. |
| 8. | Lever-1 |

-continued

| PART NUMBERS AND NAMES | |
| --- | --- |
| 9. | Lever-2. |
| 10. | Adaptor-3. |
| 11. | Lever-3. |
| 12. | Free-Wheel Adaptor-4. |
| 13. | Rod-Extension. |
| 14. | Rod-Extension2. |
| 15. | Compression Spring-1. |
| 16. | Compression Spring-2. |
| 17. | Rear Plug |
| 18. | Upper Jaw Blade. |
| 19. | Lower Jaw Blade. |
| 20. | Rod |
| 21. | Sheath. |
| 22. | Pins. |

DETAILED DESCRIPTIONS OF THE DRAWINGS

Sheet 1—

Sheet 2—

Sheet 3—

FIG. 8 is an exploded view of the handle sub-assembly, showing its main components. 3 is a ball. 4 is a washer used for retaining one end of the spring. 5 is a mini-screw for attaching to 6, the Adaptor-1 to the right rod. 7 is the Adaptor-2 for attaching 8 the Lever-1 for the index finger. 9 is the rotation Lever-2 inside the Angled Slot. 10 is the Adaptor-3 for attaching Lever-2 to the sheath of the left rod. 11 is the Lever-3 for controlling horizontal motion of the entire donor grasper, which is attached to 12, the free-wheeling adaptor, which is trapped between the two rod-extensions. 13 is the Rod Extension, with a female connection at the end with the flange. 14 is a short replica of the rod-extension, called Rod-Extension2, with a female connection at the flange, and a male connection at the other end. 15 and 16 are compression springs. 17 is the Rear Plug, which has a through hole for the Rod-extension, and a blind slot for hiding the ball joint.

Sheet 4—

Sheet 5—

Sheet 6—

Sheet 7—

Sheet 8—

Sheet 9—

Shows the views of the different positions of the jaws in one cycle of operation:

Sheet 10—

Demonstrates the different positions of the jaws and the instrument in the tying process:

Sheet 12—

Sheet 13—

DETAILED DESCRIPTION OF THE PREFERRED EMBODIMENT

Assembly Sequence:

The assembly begins with assembling the grasper sub-assemblies. The upper and lower jaws, are combined with their rods and their sheaths to form the right (1) and left (2) grasper sub-assemblies. The front-spacer is then mounted on to them, followed by the main sheath from the rear to the front. The rear-spacer is then mounted from the rear, completing the "main sub assembly". Adhesives are applied. Note, the main sheath is trapped between the shoulders on the two spacers. Sheath-1 is then locked down with the mini-screw onto the rear spacer, so it becomes stationary. Adaptor-2, Adaptor-1 with a mini-screw, spring-1, the washer and the ball are mounted onto rod-1. Adaptor-3, spring-2, rod-extension2, free-wheel adaptor, and the rod-extension—are all mounted onto rod-2. The adaptors are locked down.

The completed "main sub-assembly" is then gently inserted into the rear end of the chamber located on the top of the stationary handle and is locked down with mini-screws. The movable handle is brought in and the recess on its upper end makes a joint with the ball. The rear plug (different from the rear spacer) is mounted last and is locked down with a screw on the underside of its flange. The 3 levers are attached to their respective adaptors. The screw of the rotating lever is adjusted to allow the jaws of the donor grasper to be orientated to the vertical position, with the lever in the maximal down position.

General Comments:

1. To tie a knot with this instrument, it is necessary first to use a second regular instrument in the surgeon's other hand, to first steady the tail strand of the suture.
2. The reason for having two mini-graspers side by side within this instrument, is to facilitate trapping the tail end of the suture in the gap between them, and the passing of the head end of the suture from one to the other.
3. It is necessary for the donor grasper to first grasp the head end of the suture, before trapping the tail end of the suture, because the reverse does not work.
4. One of the graspers is intentionally given a regular scissors type of handle, in order to provide good power to the grip in the jaws in the final take-away.
5. The scissors grip usually involves having the thumb inside the "thumb loop". However, in this instrument, the thumb is not required to be placed inside the "thumb loop" until the final take-over. For most of the time, the thumb is placed on the side of the tubular chamber, like in a pistol grip, so it could actuate the controls.
6. The second grasper does not have a handle as it must be able to rotate and to slide. Its gripping power must therefore come a compression spring.
7. The present design enables the thumb to be used for multiple purposes; for sliding and for rotation of the entire instrument, for opening the jaws of the donor grasper, and for applying the scissors grip. The index finger is on the "wrong" side of the handle and can only be utilized as a trigger for closing the jaws of the right-sided recipient grasper.
8. In the recipient grasper, a compression spring is used to keep the jaws open in the resting state. In the donor grasper, a compression spring is used to keep the jaws closed in the resting state and is needed to hold onto the head end of the suture during rotation. It is not very strong, so in the final take-over by the recipient grasper, the head end of the suture will be easily pulled off the jaws of the donor grasper.
9. When grasping the head end of the suture, the jaws of the donor grasper are opened by additional forward pressure from the thumb on the free-wheeling lever inside the horizontal slot, at the end of its forward travel.
10. The top of the Movable Handle bears a receptacle for the Ball Joint, which Is intentionally hidden within the body of the stationary handle, to avoid it being interfered by the thumb.
11. The rotation and counter-rotation of the donor grasper are automatically produced by the forward and backward movements, due to the angled slot, and the lever moving in it.
12. The free-wheeling lever is designed so it is un-affected by rotation of the left-sided donor grasper. 13. The forward sliding and the simultaneous rotation are needed to keep the gap between the tip of the two graspers free, as otherwise the grasped suture will interfere with the entry into the gap by the tail strand of the suture. The backward sliding and the simultaneous de-rotation will result in placing the head end of the suture inside the jaws of the receiving grasper.
14. Previously the forward movement of the donor grasper and the opening of its jaws was created by a button at the rear, but this was difficult for the thumb to reach. This is now replaced by a lever placed on the left side of the chamber, in a better ergonomic position for the thumb, but requiring the lever's attachment to be free-wheeling.
15. The recipient grasper's jaws may be closed in one of 3 ways—using the scissors grip, or using the palm squeezing on the movable handle, or using the index finger pulling the trigger on the underside of the handle.

The invention claimed is:

1. A laparoscopic surgical instrument capable of tying a knot in a free strand of suture intra-abdominally comprising:
two small diameter laparoscopic graspers whose shafts are housed within a common external sheath, each having operating mechanisms housed within a common tubular chamber at the top of a stationary member of a scissors type of handle assembly, with only one grasper of said two graspers connected to a movable handle of said handle assembly, and acting as a recipient grasper; and a second grasper of said two graspers not connected to a movable handle but being rotatable, slideable, and acting as a donor grasper, the surgical instrument further comprising:

a narrow gap between tips of said two graspers necessary for trapping a tail strand of said suture;

a first lever extending within a horizontal slot on a side-wall of said tubular chamber for controlling forward and backward sliding of the entire said donor grasper; said first lever having a free-wheel connection to said donor grasper, thus allowing rotation as well as forward or backward sliding of said donor grasper;

a second lever within a separate angled slot on said side-wall of said tubular chamber for controlling rotation of said donor grasper; with said second lever moving within said angled slot, producing automatic simultaneous rotation and/or de-rotation of said donor grasper during its forward or backward motion;

a compression spring, said compression spring biasing an upper jaw of said donor grasper towards a closed position;

a second compression spring biasing the jaws of said recipient grasper towards an open position.

2. A method of tying a knot in a free length of suture laparoscopically and intra-abdominally comprising:

providing the laparoscopic instrument of claim 1;

providing a suture having a head end and a tail end;

passing the head end of the suture from the jaws of said donor grasper to the jaws of said recipient grasper, across and behind the tail end of said suture thereby forming a knot steadying said tail end of said suture with a separate laparoscopic grasper in a surgeon's hand not holding said laparoscopic instrument;

pushing said donor grasper forwards with the thumb of said hand, which by virtue of the angled slot, automatically and simultaneously rotates said donor grasper 90 degrees to the left, and also makes its jaws lie in a vertical Diane relative to said laparoscopic instrument, and;

applying further forward Pressure from said thumb to open the jaws of said donor grasper;

grasping the head end of said suture with the jaws of the donor grasper by releasing the forward Pressure on the thumb;

pulling back the entire laparoscopic instrument over said tail end, thereby carrying the head end of the suture with it, and advancing the entire said laparoscopic instrument forwards to trap said tail strand in said gap between the tips of the two graspers, with the tip of said donor grasper under said tail strand;

pulling back said donor grasper with the thumb on the handle, thereby automatically de-rotating its jaws 90 degrees, and placing the head end of said suture within the jaws of the said recipient grasper;

closing the jaws of the said recipient grasper, thereby taking over the head end of said suture, and Pulling it away forming the knot.

* * * * *